(12) United States Patent
Kotake et al.

(10) Patent No.: US 9,892,504 B2
(45) Date of Patent: Feb. 13, 2018

(54) IMAGE INSPECTION METHOD AND INSPECTION REGION SETTING METHOD

(71) Applicant: OMRON Corporation, Kyoto-shi, Kyoto (JP)

(72) Inventors: Yasuyo Kotake, Kyoto (JP); Yoshihisa Minato, Kyoto (JP); Yukiko Yanagawa, Nara (JP); Anh Nguyen, Kyoto (JP)

(73) Assignee: OMRON Corporation, Kyoto (JP)

( * ) Notice: Subject to any disclaimer, the term of this patent is extended or adjusted under 35 U.S.C. 154(b) by 23 days.

(21) Appl. No.: 14/383,907

(22) PCT Filed: Nov. 16, 2012

(86) PCT No.: PCT/JP2012/079831
§ 371 (c)(1),
(2) Date: Sep. 9, 2014

(87) PCT Pub. No.: WO2013/136591
PCT Pub. Date: Sep. 19, 2013

(65) Prior Publication Data
US 2015/0055823 A1 Feb. 26, 2015

(30) Foreign Application Priority Data

Mar. 14, 2012 (JP) ................................ 2012-057586

(51) Int. Cl.
*G06T 7/00* (2017.01)
*G01N 21/956* (2006.01)
(Continued)

(52) U.S. Cl.
CPC ............. *G06T 7/001* (2013.01); *G01N 21/95* (2013.01); *G01N 21/956* (2013.01); *G06T 7/12* (2017.01);
(Continued)

(58) Field of Classification Search
CPC . G06T 7/001; G06T 7/12; G06T 2207/10004; G06T 2207/10024;
(Continued)

(56) References Cited

U.S. PATENT DOCUMENTS

2003/0198372 A1 10/2003 Touzawa et al.
2012/0170813 A1* 7/2012 Benayad-Cherif ... G06T 7/0004
382/103
(Continued)

FOREIGN PATENT DOCUMENTS

JP H1183435 * 9/1997 ............. G01B 11/00
JP 2000163579 * 11/1998 ............. G01B 11/24
(Continued)

OTHER PUBLICATIONS

International Search Report for corresponding International Application No. PCT/JP2012/079831, dated Dec. 18, 2012 (2 pages).
(Continued)

*Primary Examiner* — Amandeep Saini
(74) *Attorney, Agent, or Firm* — Osha Liang LLP

(57) ABSTRACT

An image inspection method executed by an image inspection apparatus includes an acquisition step of acquiring an inspection target object image obtained by capturing an image of an inspection target object, a setting reading step of reading, from a storage device that stores inspection region defining information in advance, the inspection region defining information, an inspection region extraction step of extracting, as an inspection region image, a portion to be an inspection region from the inspection target object image, based on the inspection region defining information, and an inspection processing step of performing inspection on the inspection target object by analyzing the inspection region image. The inspection region defining information comprises information defining an initial contour of the inspec-
(Continued)

tion region and information defining a range based on the initial contour as a search range for searching a contour of the inspection region.

14 Claims, 13 Drawing Sheets

(51) Int. Cl.
*H05K 13/08* (2006.01)
*G01N 21/95* (2006.01)
*G06T 7/12* (2017.01)
*H05K 3/34* (2006.01)
*G01N 21/84* (2006.01)

(52) U.S. Cl.
CPC ..... *H05K 13/08* (2013.01); *G01N 2021/8466* (2013.01); *G01N 2021/95638* (2013.01); *G06T 2207/10004* (2013.01); *G06T 2207/10024* (2013.01); *G06T 2207/10116* (2013.01); *G06T 2207/20101* (2013.01); *G06T 2207/20104* (2013.01); *G06T 2207/20116* (2013.01); *G06T 2207/30108* (2013.01); *G06T 2207/30141* (2013.01); *H05K 3/3442* (2013.01)

(58) Field of Classification Search
CPC . G06T 2207/10116; G06T 2207/20101; G06T 2207/20104; G06T 2207/20116; G06T 2207/30108; G06T 2207/30141; G01N 21/95; G01N 21/956; G01N 2021/8466; G01N 2021/95638; H05K 13/08; H05K 3/3442
USPC .......................................................... 382/103
See application file for complete search history.

(56) References Cited

U.S. PATENT DOCUMENTS

| | | | |
|---|---|---|---|
| 2013/0010081 A1* | 1/2013 | Tenney | G05B 19/4086 348/47 |
| 2013/0170757 A1* | 7/2013 | Shinoda | G06K 9/00 382/209 |
| 2015/0228063 A1* | 8/2015 | Minakawa | H01J 37/244 382/151 |

FOREIGN PATENT DOCUMENTS

| | | |
|---|---|---|
| JP | 11-83435 A | 3/1999 |
| JP | 2000-163579 A | 6/2000 |

OTHER PUBLICATIONS

Cootes, C.J. et al.; "Active Shape Models—Their Training and Application;" Computer Vision and Image Understanding, vol. 61, No. 1; Jan. 1995; pp. 38-59 (12 pages).

Office Action in counterpart Chinese Patent Application No. 201280071322.4 dated Oct. 17, 2016 (19 pages).

T. Ling; "Research on Three-Dimensional Visualization Realization Technology Based on Medical Fault Image"; Doctoral Dissertation 1028703 05-005; Nanjing University of Aeronautics and Astronautics, College of Automation; Nanjing, China; Mar. 2015 (20 pages).

Office Action issued in corresponding Chinese Application No. 201280071322.4, dated Apr. 7, 2017 (31 pages).

Kang, Dong Joong; "A fast and stable snake algorithm for medical images," Elsevier Science B.V.; Sep. 11, 1998 (6 pages).

* cited by examiner (a)

(b)

IMAGE INSPECTION METHOD AND INSPECTION REGION SETTING METHOD

BACKGROUND

Technical Field

The present invention relates to an image inspection method and an inspection region setting method for performing appearance inspection with an image.

Background Art

For automation and labor savings for inspection in production lines, image inspection apparatuses that perform appearance inspection with an image have been widely used. Various types and methods of appearance inspection are available. In the basic configuration for the inspection, the desired inspection (for example, good/bad determination, sorting, or information acquisition) is performed by capturing an image of an inspection target object with an image sensor (camera), extracting a portion as an inspection region from the acquired image, and analyzing/evaluating the features of an image of the portion of the inspection region.

Image inspection apparatuses of this type need preparation work such as setting the inspection region, before inspection processing can be initiated. In a general apparatus, a dedicated tool for setting the inspection region is prepared, and the user himself or herself can use the tool to set an appropriate inspection region suitable for the inspection target object and an objective of the inspection. In recent years, there has been an increasing demand for minimizing setup time for improving the efficiency in small lot production of many kinds products. Thus, it is not preferable to take a long time for setting the inspection region. On the other hand, there has also been a strong demand for accurately fitting the inspection region to a portion to be the inspection target, to deal with a more complex product shape and more sophisticated and detailed inspection content, and to improve the accuracy and reliability of the inspection.

Some inspection target object might have individual difference in shape or have position/posture/scale varying in an image. For example, inspection of vegetables conveyed on a belt conveyer is considered. Vegetables all differ in shape, and cannot be accurately positioned. Thus, the position and the posture in the image differ among the inspection target objects. Furthermore, in the inspection of an industrial product such as a component mounting board, in a strict sense, the shape and the position of the components are not the same. Thus, to perform the inspection with high accuracy, the inspection region needs to be set for each inspection target object, or mismatch of the inspection region set in advance needs to be checked every time, and the inspection region needs to be set all over again, if required. These inhibit automatic inspection. When the inspection region is set to be sufficiently narrower than the inspection target object, the inspection region is less likely to be affected by the individual difference and the variation. Thus, the automatic inspection can be performed with the same inspection region. However, in the method, some portion might be excluded from the inspection region, and thus the method might lead to unsatisfactory inspection. A countermeasure of setting the range of the inspection region to be sufficiently large with respect to the inspection target object may be taken. However, with the method, the inspection region includes pixels of a portion (a background and other objects, for example) that has nothing to do with the inspection target object. Such pixels become noise, and thus, the inspection accuracy is degraded.

As a method for automatically setting the inspection region, an inspection region extraction method utilizing binarization and color gamut extraction, has conventionally been known. Specifically, the method includes extracting a pixel group, corresponding to a brightness range and color gamut set in advance, from an image, and setting the pixel group as the inspection region. The method is effective when there is a high contrast in brightness or a color between a portion (foreground) to be extracted as the inspection region and other portions (background). However, shading on the foreground portion due to lighting and the like, the foreground portion including various levels of brightness or various colors, and the background including a color that is similar to that of the foreground portion might make the accurate extraction of only the foreground portion difficult with the binarization and the color gamut extraction. In recent years, the inspection content has become highly sophisticated and more detailed. For example, there are many cases with almost no color difference between the foreground and the background, such as the surface inspection on only a single cutting surface in a molded component, and inspection on a single component on only a printed circuit board, on which a number of components are mounted. The binarization and the color gamut extraction are performed for each pixel in an image, and thus are likely to be affected by noise and change in lighting. The extracted inspection region might lack some pixels, or, conversely, pixels in the background portion might be selected as if some outlier is formed. Thus, the inspection accuracy is degraded.

Non Patent Literature 1 proposes a method of automatically extracting a contour of a target object (person or object) in an image. In the method, a shape model defining the contour shape of the target object is prepared, and is fit to the target object in an input image. Here, a calculation is repeated to minimize the error, by using the relationship between a position/posture/rotation parameter of the shape model and the feature quantity of the target object, as an evaluation value, so as to be capable of corresponding to the contour of a target object having a variable shape and position. In the method of Non Patent Literature 1, the processing of fitting the contour of the shape model to the target object in the input image is performed, based on the distribution of pixel values in the direction orthogonal to the contour line of the shape model. Here, the calculation needs to be repeated for a large number of times to minimize the shape model and the amount of information around the contour point of the target object, and thus, the calculation cost is extremely high.

CITATION LIST

Non Patent Literature

NPL 1: T. F. Cootes, C. J. Taylor, D. H. Cooper, et al., "Active Shape Models—Their Training and Application," Computer Vision and Image Understanding, Vol. 61, No. 1, January, pp. 38 to 59, 1995.

SUMMARY

One or more embodiments of the present invention provides a technique of accurately and promptly perform processing of automatically adjusting an inspection region, in accordance with an individual difference of an inspection target object in shape and variation of the position/posture/ scale of the inspection target object in an image, and thereby enabling highly accurate inspection.

According to one or more embodiments of the present invention, an image inspection apparatus is provided with an initial contour of an inspection region and a search range (range within which variation of the contour is allowed) as inspection region defining information. When the inspection target object is inspected, edge points are detected from the search range through edge search processing. The edge points are connected or approximated to individually determine the inspection region for each inspection target object.

Specifically, according to one or more embodiments of the present invention, an image inspection method is executed by an image inspection apparatus, and the method includes: an acquisition step of acquiring an inspection target object image obtained by capturing an image of an inspection target object; a setting reading step of reading, from a storage device that stores inspection region defining information in advance, the inspection region defining information; an inspection region extraction step of extracting, as an inspection region image, a portion to be an inspection region from the inspection target object image, based on the inspection region defining information; and an inspection processing step of performing inspection on the inspection target object by analyzing the inspection region image. The inspection region defining information includes information defining an initial contour of the inspection region and information defining a range based on the initial contour as a search range for searching a contour of the inspection region. The inspection region extraction step includes: a base point setting step of setting a plurality of base points on the initial contour; an edge searching step of performing edge search processing on a line that passes through each base point and intersects with the initial contour, within an region of the search range of the inspection target object image, to determine an edge point corresponding to each base point; and a contour generation step of connecting or approximating a plurality of the edge points respectively corresponding to the plurality of base points to generate a contour of the inspection region of the inspection target object image.

With this configuration, the contour of the inspection region can be deformed to fit the edge of the inspection target object in an image through the edge search processing based on the initial contour. Thus, even when there is an individual difference in shape, or the position/posture/scale in an image might vary, the inspection region can be adaptively and automatically adjusted, in accordance with such individual difference and variation of the inspection target object. Furthermore, because the range in which the edge searching is performed is defined in advance, the time required for searching and determining the edge points, and the time required for generating the contour and extracting the inspection region can be shortened. Thus, the inspection that is faster and more accurate than a conventional case can be achieved.

In the edge searching step, when a plurality of edge point candidates are detected on a line passing through a certain base point, any one of the edge point candidates is selected. Methods for the selection include the following for example. In one method, one of the plurality of candidates, closest to the base point is selected as the edge point corresponding to the base point. A more accurate result can be obtained with this method, in a case of an inspection target object with not so large individual difference and variation. As another selection method according to one or more embodiments of the present invention, one of the plurality of candidates with a distance from the base point closest to a distance between a peripheral base point in a periphery of the base point and a peripheral edge point corresponding to the peripheral base point, is selected as the edge point corresponding to the base point. A more accurate result can be obtained by focusing on the edge points in the peripheral portion as in this method, in a case of an inspection target object with relatively large individual difference and variation.

In the edge searching step, no edge point might be detected from a line passing through a certain base point. As exceptional processing in this case, for example, a method of setting an edge point corresponding to the base point at the position that is the same as the base point, and a method of interpolating a plurality of peripheral edge points respectively corresponding to a plurality of peripheral base points in the periphery of the base point to obtain the position of the edge point corresponding to the base point, may be employed. A more accurate result can be obtained with the former method in a case of the inspection target object with a relatively small individual difference and variation, and with the latter method in a case of the inspection target object with a relatively large individual difference and variation.

In the edge searching step according to one or more embodiments of the present invention, a range in which an edge point corresponding to a certain base point is searched is obtained by narrowing down the search range, based on a position of the peripheral edge point corresponding to a peripheral base point in the periphery of the base point. Alternatively, according to one or more embodiments of the present invention, the edge searching step includes a rough searching step of determining a corresponding edge point for a plurality of base points sparsely disposed on the initial contour, and a detailed searching step of determining the corresponding edge point for a plurality of base points more densely disposed than in the rough searching step. According to one or more embodiments of the present invention, in the detailed searching step, a range in which an edge point corresponding to a certain base point is searched is obtained by narrowing down the search range, based on a position of the edge point determined in the rough searching step. By thus narrowing down the edge searching range through these processing, the time required for searching and determining the edge point can be further shortened.

According to one or more embodiments of the present invention, in the contour generating step, whether a generated contour is included within the search range is determined, and when the contour has a portion outside the search range, the contour is corrected so that the portion is included within the search range. Thus, the contour of the inspection region can be prevented from being set at a position unintended by a user.

One or more embodiments of the present invention is an inspection region setting method for setting the inspection region defining information for an image inspection apparatus configured to execute the image inspection method described above. The method includes: an acquisition step, in which a computer acquires a sample image of an inspection target object and an inspection region set to the sample image; a contour extraction step, in which the computer extracts a contour of the inspection region; a range setting step, in which the computer allows a user to set a range in which the contour of the inspection region is variable; and a defining information generating step, in which the computer generates inspection region defining information including information defining an initial contour and information defining a search range, based on the contour of the inspection region and the range set by the user.

With this method, the inspection region defining information required for the inspection region extraction (edge search) in the image inspection apparatus can be easily set (generated).

In the range setting step, according to one or more embodiments of the present invention, different ranges are settable at positions on the contour of the inspection region. This enables, for example, a flexible range setting of setting a wide search range for a portion with a large variation of position, shape, and the like, and setting a narrow search range for a portion with small variation or not allowing large variation. As a result, the time required for the inspection region extraction (edge searching) in the image inspection apparatus is optimized, and processing time can be shortened.

The information defining the initial contour according to one or more embodiments of the present invention includes information defining positions of the plurality of base points set on the initial contour when the edge search processing in the image inspection method is performed. Thus, the setting of the base points in the edge search processing is facilitated, and the processing time can be shortened. Here, according to one or more embodiments of the present invention, the inspection region setting method further includes: a step, in which the computer allows the user to set a quantity, interval, or arrangement of base points; and a step, in which the computer determines the positions of a plurality of the base points set on the initial contour, based on the quantity, the interval, or the arrangement of the base points set by the user.

One or more embodiments of the present invention may be regarded as an image inspection apparatus including at least any of the means, and as an inspection region setting device for the image inspection apparatus including at least any of the means related to the inspection region setting. One or more embodiments of the present invention may be regarded as an image inspection method or an inspection region setting method of executing at least any one of the processes, a program for causing the image inspection apparatus or a computer to execute the method, and a storage medium storing the program.

According to one or more embodiments of the present invention, processing of automatically adjusting an inspection region can be promptly and accurately performed, in accordance with the individual difference of an inspection target object in shape and variation of a position/posture/scale of the inspection target object in an image, whereby highly accurate inspection can be achieved.

DETAILED DESCRIPTION

Embodiments of the present invention will be described below with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. One or more of the embodiments described below relate to an image inspection apparatus that performs appearance inspection with an image, and to an inspection region setting device for supporting an operation for generating inspection region defining information provided to the image inspection apparatus. The image inspection apparatus is favorably used for application such as automatic or semiautomatic continuous inspection on a number of articles on a production line in FA and the like. The article as the inspection target may be of any type. The image inspection apparatus of one or more embodiments adaptively determines the inspection region for each inspection target object by using an original image captured by an image sensor, and thus can be particularly favorably applied to a case where the position/shape of the inspection region in the original image varies among the inspection target objects. There are various objectives of and various inspection items in the appearance inspection, and the inspection region setting device of one or more embodiments can be favorable applied to any inspection. In one or more embodiments, the inspection region setting device is mounted as a function (setting tool) of an image inspection apparatus. Alternatively, the image inspection apparatus and the inspection region setting device may be separately formed.

<First Embodiment>

(Image Inspection Apparatus)

Figure 1:
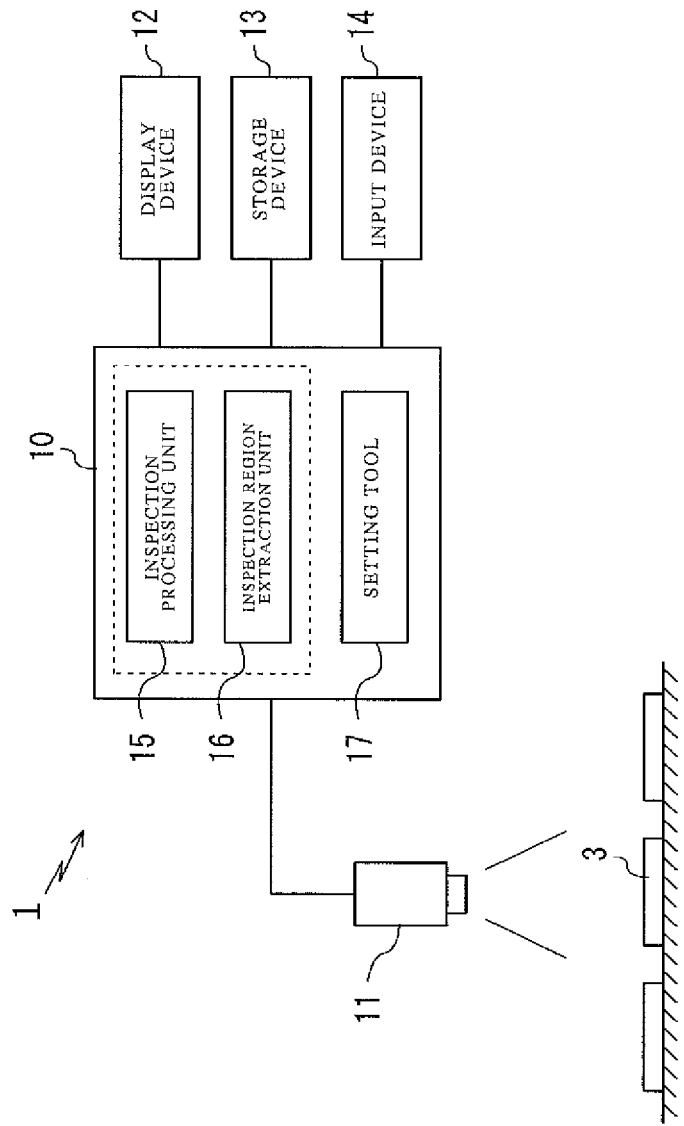
FIG. 1 is a diagram schematically showing the configuration of an image inspection apparatus.

FIG. 1 schematically shows the configuration of an image inspection apparatus. An image inspection apparatus 1 is a system that performs appearance inspection on an inspection target object 3 conveyed on a conveyance path.

As shown in FIG. 1, the image inspection apparatus 1 includes hardware such as an apparatus main body 10, an image sensor 11, a display device 12, a storage device 13, and an input device 14. The image sensor 11 is a device for capturing a color or monochrome still or moving image into the apparatus main body 10. For example, a digital camera can be suitably used as the image sensor 11. When a special image (X ray image, thermo image, and the like) other than optical images is used for the inspection, a sensor suitable for such an image may be used. The display device 12 is a device for displaying an image captured by the image sensor 11, an inspection result, and a GUI screen related to inspection processing and setting processing. For example, a liquid crystal display can be used as the display device 12. The storage device 13 is a device that stores various types of setting information (inspection region defining information and an inspection logic) and the inspection result, to which the image inspection apparatus 1 refers in the inspection processing. For example, an HDD, an SSD, a flash memory, and a network storage may be used as the storage device 13. The input device 14 is a device operated by a user to input an instruction to the apparatus main body 10. For example, a mouse, a keyboard, a touch panel, and a dedicated console can be used as the input device 14.

The apparatus main body 10 may be formed of a computer including, as hardware, a CPU (central processing unit), a main storage device (RAM), and an auxiliary storage device (ROM, HDD, SSD, or the like). The apparatus main body 10 includes, as functions, an inspection processing unit 15, an inspection region extraction unit 16, and a setting tool 17. The inspection processing unit 15 and the inspection region extraction unit 16 are functions related to the inspection processing, and the setting tool 17 is a function for supporting a work performed by the user to set the setting information required for the inspection processing. The functions are implemented when a computer program stored in the auxiliary storage device or the storage device 13 is loaded onto the main storage device, and executed by the CPU. FIG. 1 shows merely an example of the apparatus configuration. All or a part of the image sensor 11, the display device 12, the storage device 13, and the input device 14 may be integrated with the apparatus main body 10. The apparatus main body 10 may be formed of a computer such as a personal computer or a slate terminal, or may be formed of a dedicated chip, an onboard computer or the like.

(Inspection Processing)

Figure 2:
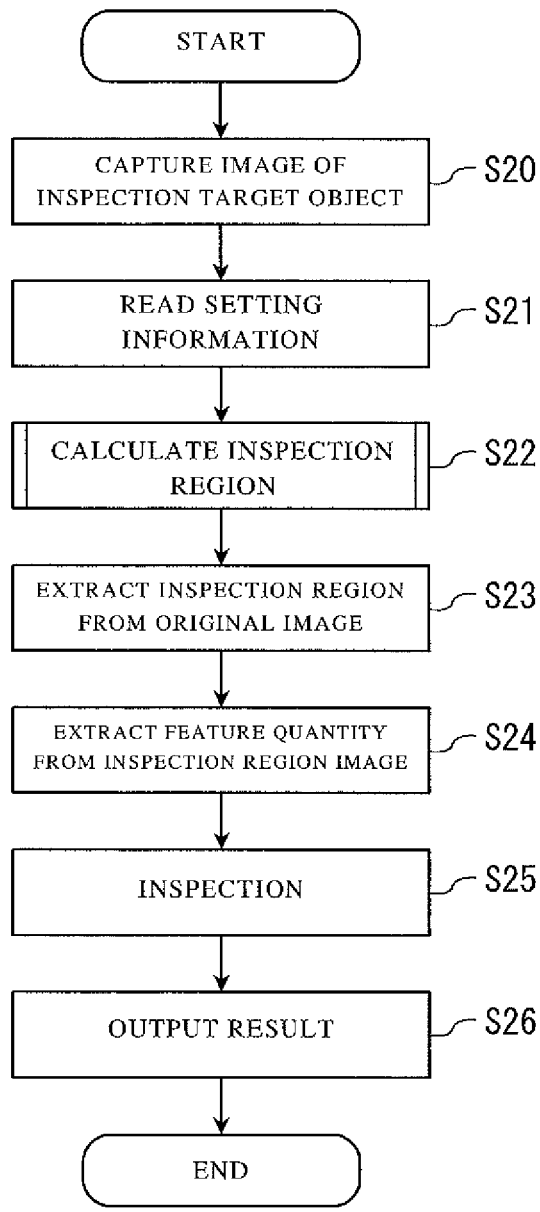
FIG. 2 is a flowchart showing a flow of inspection processing.
Figure 3:
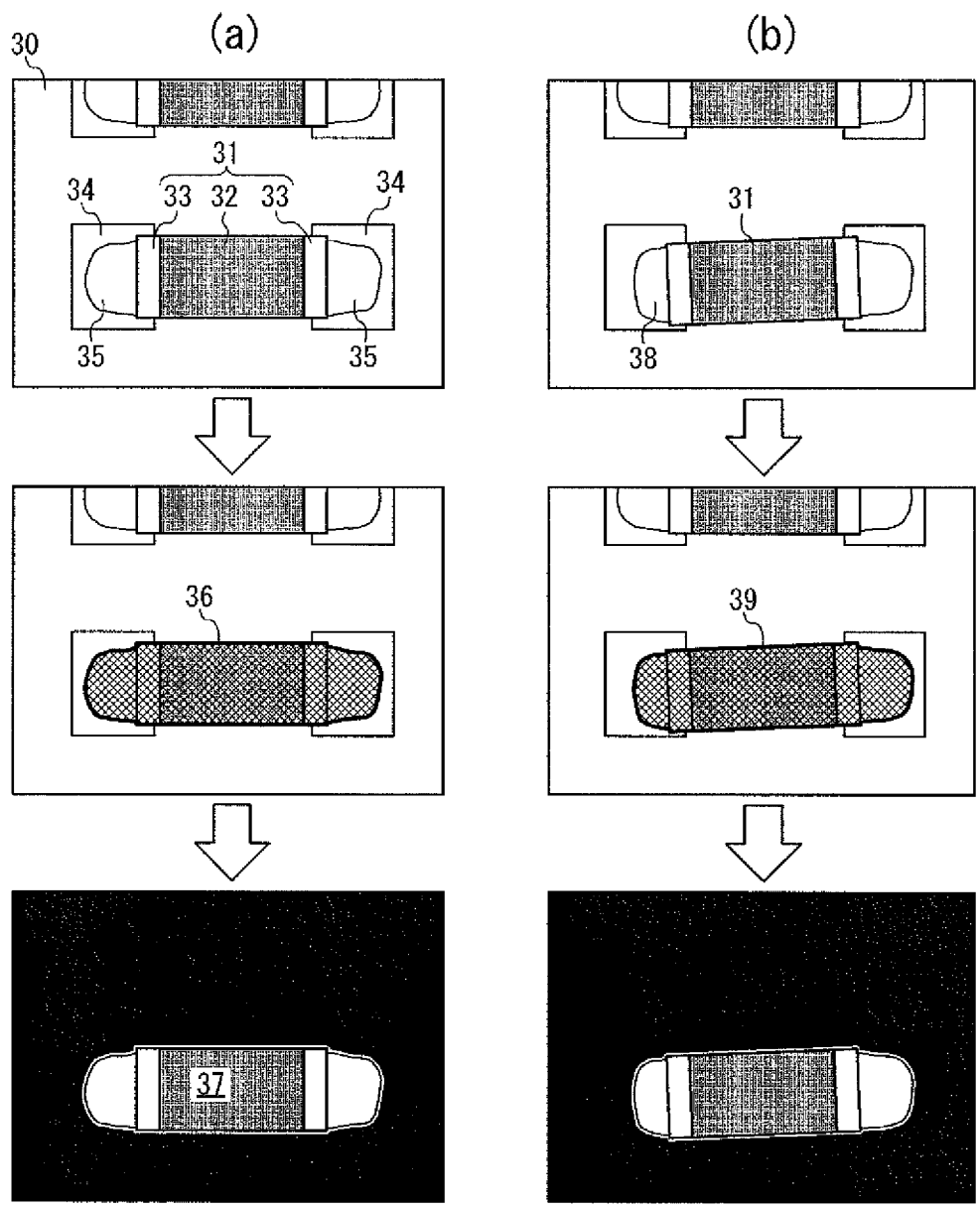
FIGS. 3(a)-(b) are diagrams for describing a process of extracting an inspection region in the inspection processing.

Operations related to the inspection processing performed by the image inspection apparatus 1 will be described by referring to FIGS. 2 and 3. FIG. 2 is a flowchart showing a flow of the inspection processing. FIGS. 3(a)-(b) are diagrams for describing a process of extracting an inspection region in the inspection processing. Here, for convenience of explanation, the flow of the inspection processing is described with inspection on the positioning/posture/soldering and the like, of electronic components on a printed circuit board, as an example.

In Step S20, the image sensor 11 captures an image of the printed circuit board 30, and the image data is captured into the apparatus main body 10. When an image captured in advance is in the auxiliary storage device or the storage device 13 of the apparatus main body 10, data to be the inspection target may be read from the auxiliary storage device or the storage device 13. Here, the captured image (original image; inspection target object image) is displayed on the display device 12, as appropriate. The upper section of FIG. 3(a) shows an example of the original image. The original image includes an electronic component 31 as the inspection target object. A neighboring electronic component partially appears above the electronic component 31. The electronic component 31 includes electrodes 33 on both sides of a component main body 32. The electrodes 33 are each soldered on a land 34 of a printed circuit board 30. The reference sign 35 denotes a solder.

In Step S21, the inspection region extraction unit 16 reads the required setting information from the storage device 13. The setting information includes at least the inspection region defining information and the inspection logic. The inspection region defining information is the information used for processing of calculating an inspection region, in the later step. The information will be described later in detail. The inspection logic is information defining the detail of the inspection processing. For example, the inspection logic includes a type and a determination method for a feature quantity used for inspection, as well as a parameter and a threshold used for extracting the feature quantity and determination processing.

In Step S22, the inspection region extraction unit 16 uses the inspection region defining information read in Step S21 to calculate the inspection region in the original image. The middle section of FIG. 3(a) shows a state where an inspection region (illustrated in cross-hatching) 36, obtained in Step S22, is overlaid on the original image. It can be seen that the electronic component 31 and the solders 35 are selected as the inspection region 36.

In the appearance inspection using the image, according to one or more embodiments of the present invention, only pixels to be the inspection target are accurately extracted as the inspection region 36. This is because, when the inspection region 36 includes unwanted pixels, the pixels become noise that might degrade the inspection accuracy. On the other hand, when the inspection region 36 is smaller than the range to be the target of the inspection, unsatisfactory inspection might occur. The position/posture/shape of the inspection target object is not always the same. FIG. 3(b) shows an example of the inspection target object on another circuit board. In this example, the electronic component 31 is wrongly positioned and inclined, and the amount of a left side solder 38 is less than a prescribed amount. To deal with such an individual variation, in the apparatus of the first embodiment, the position/shape of the inspection region is not fixed, and the inspection region is adaptively obtained in accordance with the position/posture/shape and the like of the inspection target object in the original image. As a result, an appropriate inspection region 39 is obtained, as shown in the middle section of FIG. 3(b). The processing in Step S22 will be described in detail later.

In Step S23, the inspection region extraction unit 16 extracts a portion of the inspection region from the original image, in accordance with the inspection region obtained in Step S22. The lower section of FIG. 3(a) shows a state where only an image (inspection region image 37) of a portion of the inspection region 36 is extracted from the original image. In the inspection region image 37, the surface of the printed circuit board 30, the land 34, the neighboring electronic component, and the like, are deleted. The inspection region image 37 thus obtained is transmitted to the inspection processing unit 15.

In Step S24, the inspection processing unit 15 extracts required feature quantities from the inspection region image 37, in accordance with the inspection logic. For example, the center of gravity and the angle of the edge of the component main body 32 are extracted as the feature quantities for the inspection to see whether the position and the posture of the electronic component 31 are correct. The region and the color feature of a portion of the solder 35 are extracted as the feature quantities for the inspection to see whether soldering has been properly performed.

In Step S25, the inspection processing unit 15 performs the inspection processing, in accordance with the inspection logic. For example, the component is determined to be wrongly positioned, when the center of gravity and the edge angle of the component main body 32 obtained in Step S24, exceed the allowable value. Furthermore, it can be determined that the soldering has not been properly performed, when the area and the color feature of the solder 35 are abnormal.

In Step S26, the inspection processing unit 15 displays the inspection result on the display device 12, and stores the result in the storage device 13. Thus, the inspection processing of one electronic component 31 is completed. In a production line, the processing method above described is repeated for inspection target objects sequentially conveyed.

(Calculation of Inspection Region)

Figure 4:
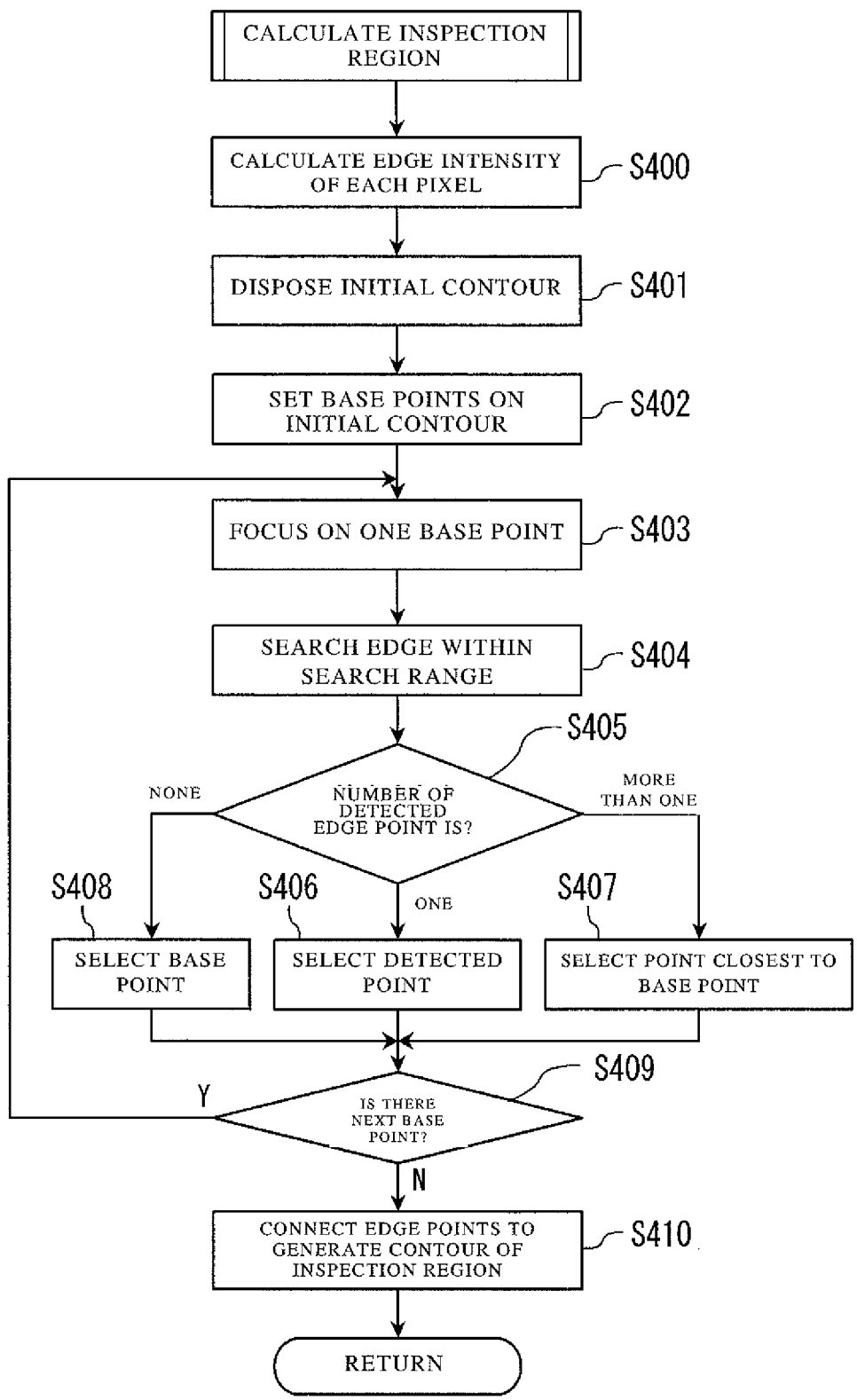
FIG. 4 is a flowchart showing processing of calculating the inspection region in detail.
Figure 5:
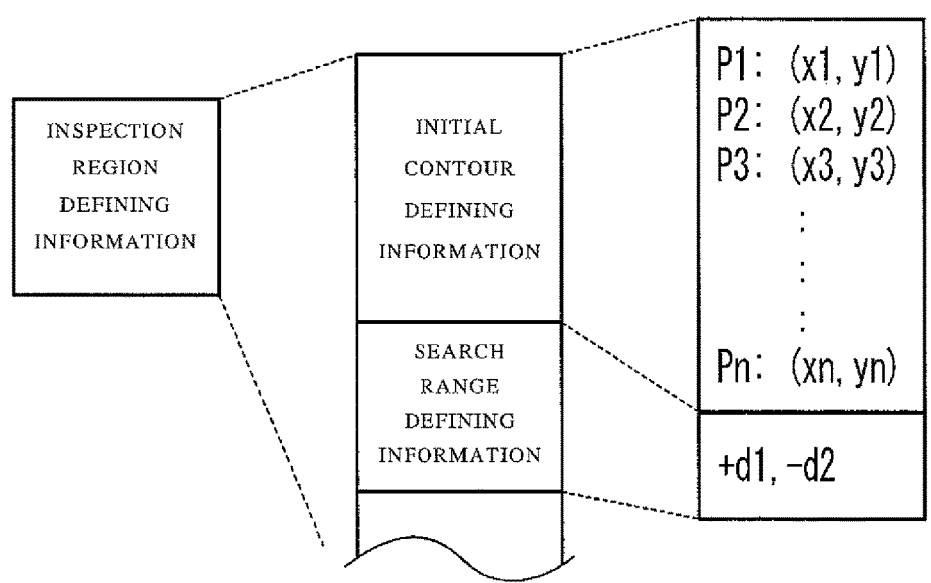
FIG. 5 is a diagram schematically showing the configuration of inspection region defining information.
Figure 6:
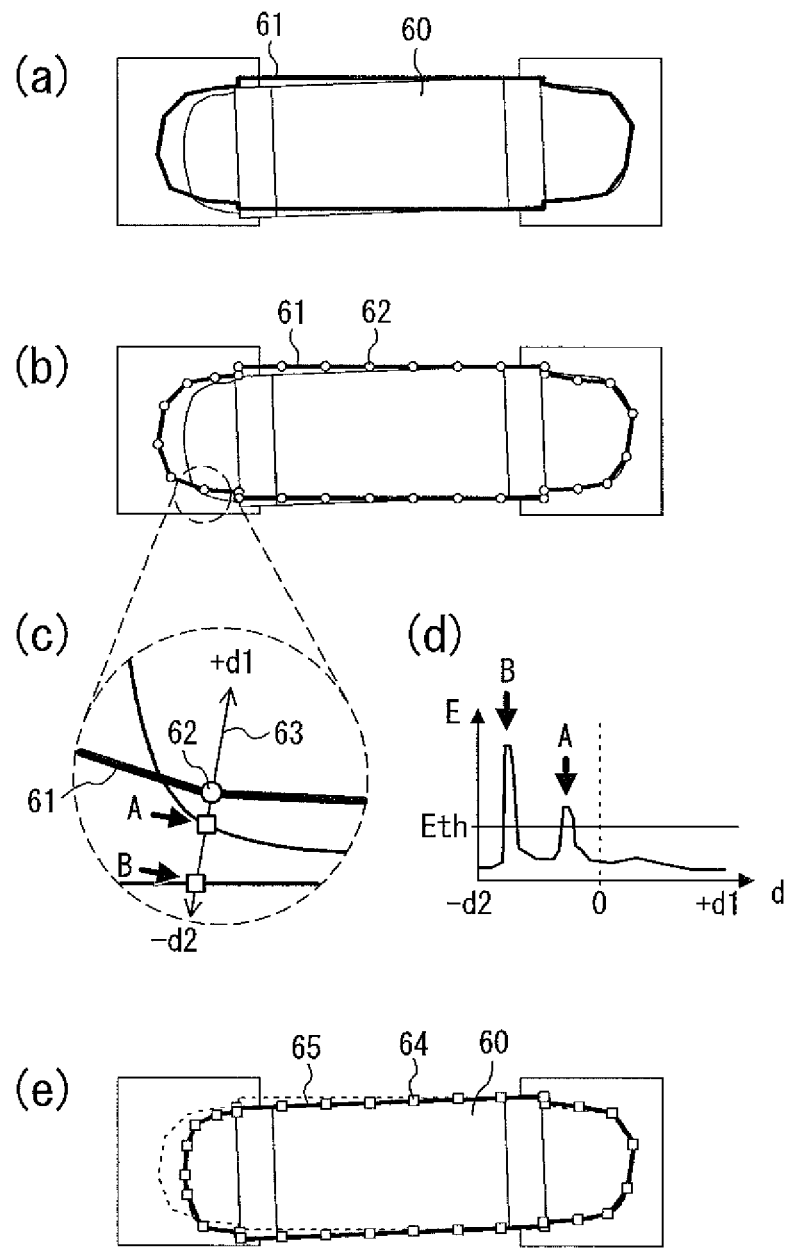
FIGS. 6(a)-(e) are diagrams conceptually showing the processing of calculating the inspection region.

The processing of calculating the inspection region, in Step S22 in FIG. 2, will be described by referring to FIG. 4, FIG. 5, and FIGS. 6(a)-(e). FIG. 4 is a flowchart showing the processing of calculating the inspection region, in detail. FIG. 5 is a diagram schematically showing the configuration of the inspection region defining information. FIGS. 6(a)-(e) are diagrams conceptually showing the processing of calculating the inspection region.

As shown in FIG. 5, the inspection region defining information read in Step S21 includes initial contour defining information and search range defining information. The initial contour defining information defines the initial contour of the inspection region (also referred to as reference contour). In the first embodiment, the initial contour defining information includes data on a sequence of a plurality of (n) points P1, P2, ..., Pn on the contour line. The search range defining information is information defining a range from the initial contour as the search range for searching the contour of the inspection region. In other words, the search range defining information defines the range in which the variation of the contour in the inspection region is allowed. In the first embodiment, the search range in the positive and the negative directions is defined with the relative number of pixels from the initial contour, with the directions towards the inner and the outer sides of the inspection region respectively defined as positive (+) and negative (−) directions. In the example of FIG. 5, the range from d1 pixels to d2 pixels respectively toward the inner and the outer sides of the initial contour is defined as the search range.

By following the flowchart in FIG. 4, the flow of the processing of calculating the inspection region will be explained.

First, the inspection region extraction unit 16 calculates the edge intensity of all the pixels in the original image (Step S400). The edge intensity is an index representing the likelihood of the pixel as the edge. For example, the differential value, of the pixel value (concentration value), at the pixel, can be used as the edge intensity. In the first embodiment, a Sobel filter is used on the original image, in the X and Y directions, to generate an edge image. An edge intensity E (x, y) of a pixel (x, y) is obtained by the following formula:

$$E(x, y) = \sqrt{Sx(x,y)^2 + Sy(x,y)^2}$$ [Formula 1]

Here Sx (x,y) is an edge image generated by using the Sobel filter in the X direction. Sy (x,y) is an edge image generated by using the Sobel filter in the Y direction. This method for calculating the edge intensity is merely an example. Other differential filters can be used, and a differential filter, in at least three directions, can be combined.

Next, the inspection region extraction unit 16 arranges the initial contour on the original image, based on the initial contour defining information of the inspection region defining information (Step S401). FIG. 6(a) shows an example of an inspection target object 60 in the original image and an arranged initial contour 61. Here, the coordinate value of the initial contour, defined by the initial contour defining information, can be directly used. However, when the position or the posture of the inspection region might largely vary among the inspection target objects (for example, to be out of the search range), the inspection region extraction unit 16 may translate or rotate any one of the original image and the initial contour, to arrange the initial contour 61 in accordance with the inspection target object 60 in the original image. For example, such processing can be implemented with known pattern matching, or by selectively arranging the initial contour 61 by using the edge intensity generated in Step S400 in such a manner that the accumulated values of the edge intensity on the initial contour 61 is maximized.

Then, as shown in FIG. 6(b), the inspection region extraction unit 16 sets a plurality of base points 62 on the initial contour 61 (Step S402). In the first embodiment, the definition points P1, P2, ..., Pn, on the initial contour 61, are directly used as the base points 62. Furthermore, the base points and the definition points of the initial contour do not necessarily need to match. The base points may be thinned, and thus the base points less than the definition points may be set. The base points may be each added between the definition points, and thus the base points more than the definition points may be set. Alternatively, the base points may be set at any positions on the initial contour, regardless of the definition points.

Then, the inspection region extraction unit 16 executes edge search processing in Steps S403 to S409 on each of the base points set in Step S402. First, the inspection region extraction unit 16 focuses on a single base point 62 (Step S403) and checks a normal line 63 that passes through the base point 62 and is orthogonal to the initial contour 61 (see FIG. 6(c)). Then the inspection region extraction unit 16 searches for an edge point on the normal line 63 (Step S404). Here, the inspection region extraction unit 16 performs the search only in region on the inner side of the search range defined by the search range defining information. In the first embodiment, as shown in an enlarged view in FIG. 6(c), the d1 pixels are on the inner side of the inspection region and the d2 pixels are on the outer side of the inspection region, from the base point 62. Thus, the search range includes the sum of d1+d2 pixels. In FIG. 6(d), the horizontal axis represents the position on the normal line 63 (distance d from the base point 62), and the vertical axis represents the edge intensity E. In Step S404, the point with the edge intensity E exceeding a predetermined threshold Eth is selected as a candidate of the edge point corresponding to the base point 62. In this example, a point A at the boundary between the solder and the land, and a point B at the boundary between the land and the circuit board surface, are detected as edge point candidates.

Then, in Step S405, the processing is determined in accordance with the number of detected edge point candidates. If there is only one edge point candidate, this point is directly selected as the corresponding edge point (Step S406). If there is a plurality of edge point candidates, the point closest to the base point 62 is selected as the corresponding edge point (Step S407). If no edge point candidate is detected, the base point 62 is selected as the corresponding edge point (Step S408). In the case of FIG. 6(d), the point A and point B are detected as candidates, and the point A closer to the base point 62 is selected as the corresponding edge point in Step S407.

The processing in Steps S403 to S408 described above is sequentially executed on each of the base points 62 (Step S409), and thus a plurality of edge points 64, respectively corresponding to all the base points 62 on the initial contour line 61, are determined. Then, the inspection region extraction unit 16 sequentially connects the edge points 64 through a straight or a curved line, to generate a contour 65 of the inspection region (Step S410). As shown in FIG. 6(e), the contour 65 obtained as described above fits better with the outer shape of the inspection target object 60 in the original image, than the initial contour 61.

(Setting Inspection Region Defining Information)

Figure 7:
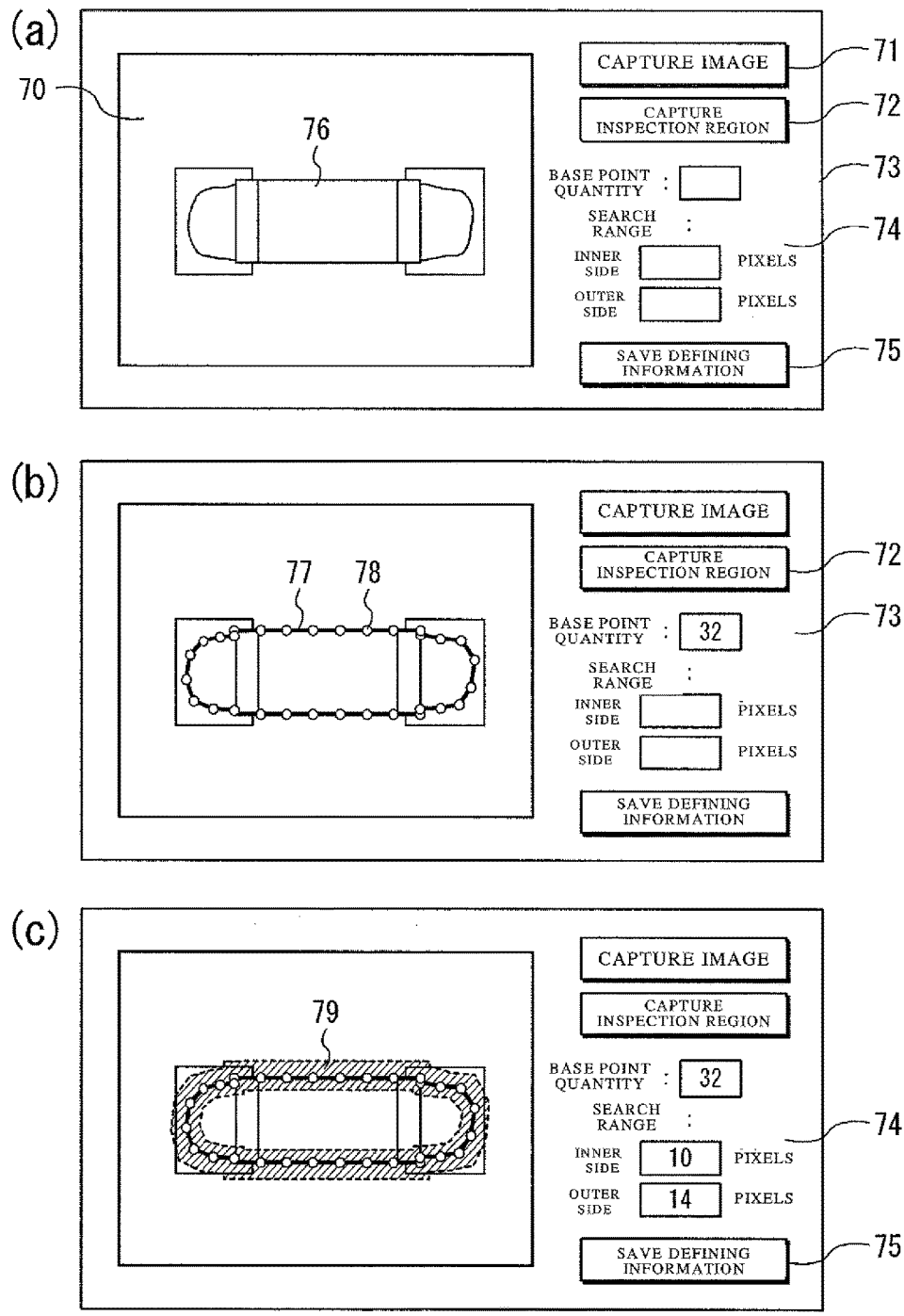
FIGS. 7(a)-(c) are diagrams showing an example of a setting screen for the inspection region defining information.

Next, the functions and operation of the setting tool 17 will be described by referring to FIGS. 7(*a*)-(*c*). FIGS. 7(*a*)-(*c*) are diagrams showing one example of a setting screen for the inspection region defining information displayed by the setting tool 17.

When the setting tool 17 is started, the setting screen in FIG. 7(*a*) is displayed on the display device 12. The setting screen includes an image window 70, an image capture button 71, an inspection region capture button 72, a base point quantity setting box 73, a search range setting box 74, and a defining information save button 75. The selection of a button and an input to a box can be performed with the input device 14. This setting screen is merely an example. Any UI can be used, as long as the parameters can be input, an inspection region can be checked, and the like operation can be performed as described below.

When the image capture button 71 is pressed, the setting tool 17 reads data on an sample image of an inspection target object from the auxiliary storage device or the storage device 13 of the apparatus main body 10. The sample image acquired herein is displayed on the image window 70 of the setting screen as shown in FIG. 7(*a*). Then, when the inspection region capture button 72 is pressed, the setting tool 17 reads data on the inspection region that has been set to the sample image, from the auxiliary storage device or the storage device 13 of the apparatus main body 10. The data of the inspection region can be of any format. For example, a bitmask with different labels respectively on the inner and outer sides of the inspection region may be used.

After reading the inspection region, the setting tool 17 extracts the contour of the inspection region, and arranges a plurality of base points on the contour line. A contour 77 of the inspection region and base points 78 are overlaid on an inspection target object 76 of the sample image to be displayed, as shown in FIG. 7(*b*). Here, by changing the value in the base point quantity setting box 73, the user can change the number of base points 78, that is, the density of the base points 78.

Then, the search range is set. The search range (pixel quantity), towards the inner and outer sides of the inspection region, can be individually set with the search range setting box 74. In FIG. 7(*c*), 10 pixels are set on the inner side and 14 pixels are set on the outer side. The search range 79 thus defined is overlaid on the sample image to be displayed.

With the screen described above displayed, the user can check the contour 77 of the inspection region, the number and the interval of the base points 78, the width of the search range 79, and the like, at a glance. Then, when the defining information save button 75 is pressed, the setting tool 17 generates the inspection region defining information (initial contour defining information and the search range defining information) as shown in FIG. 5, based on the coordinate values of the contour 77 and the base points 78, as well as the value set by the search range setting box 74. The generated inspection region defining information is stored in the storage device 13.

With the configuration of one or more embodiments described above, the contour of the inspection region can be deformed to fit the edge of the inspection target object in the image, by edge search processing based on the initial contour. Therefore, even when there are individual differences in shape, or when the position/posture/scale in an image might vary, the inspection region can be adaptively and automatically adjusted in accordance with the individual difference and the variation of the inspection target object. Moreover, because the range in which the edge search is performed is defined in advance, the time required for searching and determining the edge points, contour generation, and inspection region extraction can be shortened. Thus, the inspection can be performed faster and more accurately than in a conventional case.

In the first embodiment, when a plurality of edge point candidates are detected for a certain base point, the closest point to the base point is selected. When no edge point candidate is detected, the base point is directly selected as the edge point. With this simple algorithm (S405 to S408 in FIG. 4), the calculation cost required for searching the edge can be reduced, and high speed processing can be achieved. The processing in Steps S407 and S408 of the first embodiment (processing of selecting a base point, or the closest point to the base point), is an algorithm in which the initial contour has a high priority, and is favorably applied to an inspection target object with relatively small individual difference and variation.

In the flow of FIG. 4, all the edge point candidates for a single base point are detected (Step S404), and then the number of the edge point candidates is checked (Step S405). Alternatively, the same result can be obtained with an algorithm of sequentially searching edges, from the one closest to a base point, and terminating the search processing when one point satisfying a condition as the edge point (point exceeding the threshold Eth) is detected. An advantage in using this algorithm is that the time required for searching and determining the edge points can be further shortened.

<Second Embodiment>

Figure 8:
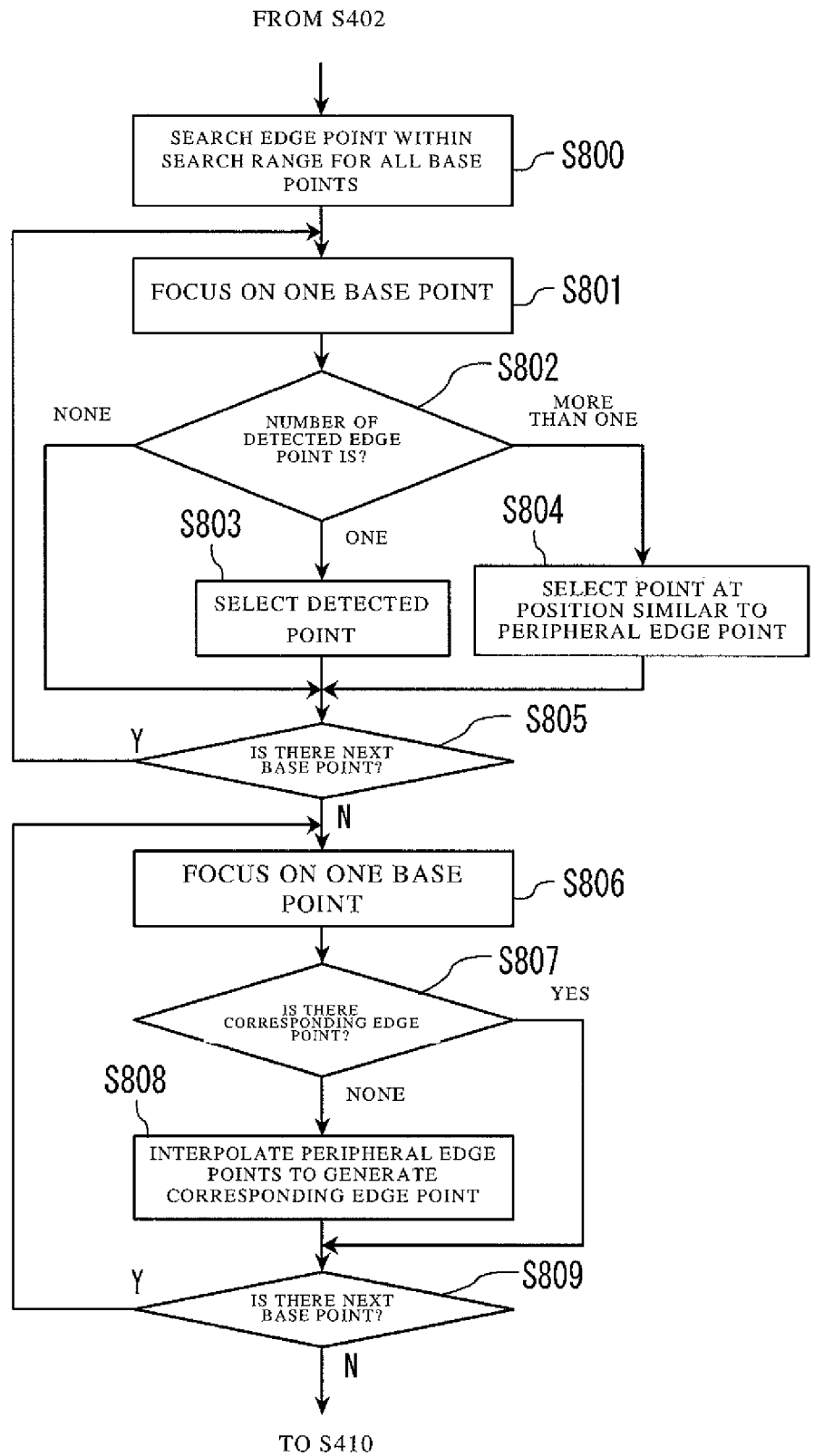
FIG. 8 is a flowchart showing processing in a second embodiment.

A second embodiment of the present invention is described by referring to FIG. 8. The differences from the first embodiment are the method of selecting the edge point when a plurality of edge point candidates are detected, and a method of processing in the case where no edge point candidate is detected. Aside from these, the configuration and the processing are the same as those in the first embodiment.

FIG. 8 is a flowchart of processing replacing that in Steps S403 to S409 in the flowchart of FIG. 4 of the first embodiment. The processing as the feature of the second embodiment is described by following the flowchart.

The inspection region extraction unit 16 calculates the edge intensity of the inspection target object image, arranges the initial contour, and sets the base points, as in the first embodiment (Steps S400 to S402). Then, the inspection region extraction unit 16 performs the processing to search the edge points sequentially for all the base points (Step S800). The algorithm for the edge searching is the same as that in Step S404 of the first embodiment.

After the edge searching for all the base points is completed, the inspection region extraction unit 16 checks the number of detected edge point candidates (Step S802), for each base point (Steps S801 and S805). When only one edge point candidate is detected, this point is directly selected as the corresponding edge point (Step S803). When a plurality of edge point candidates are detected, a candidate at a position similar to that of the edge point (peripheral edge point) detected for a peripheral base point in the periphery of the focused base point is selected as the corresponding edge point (Step S804).

Figure 9:
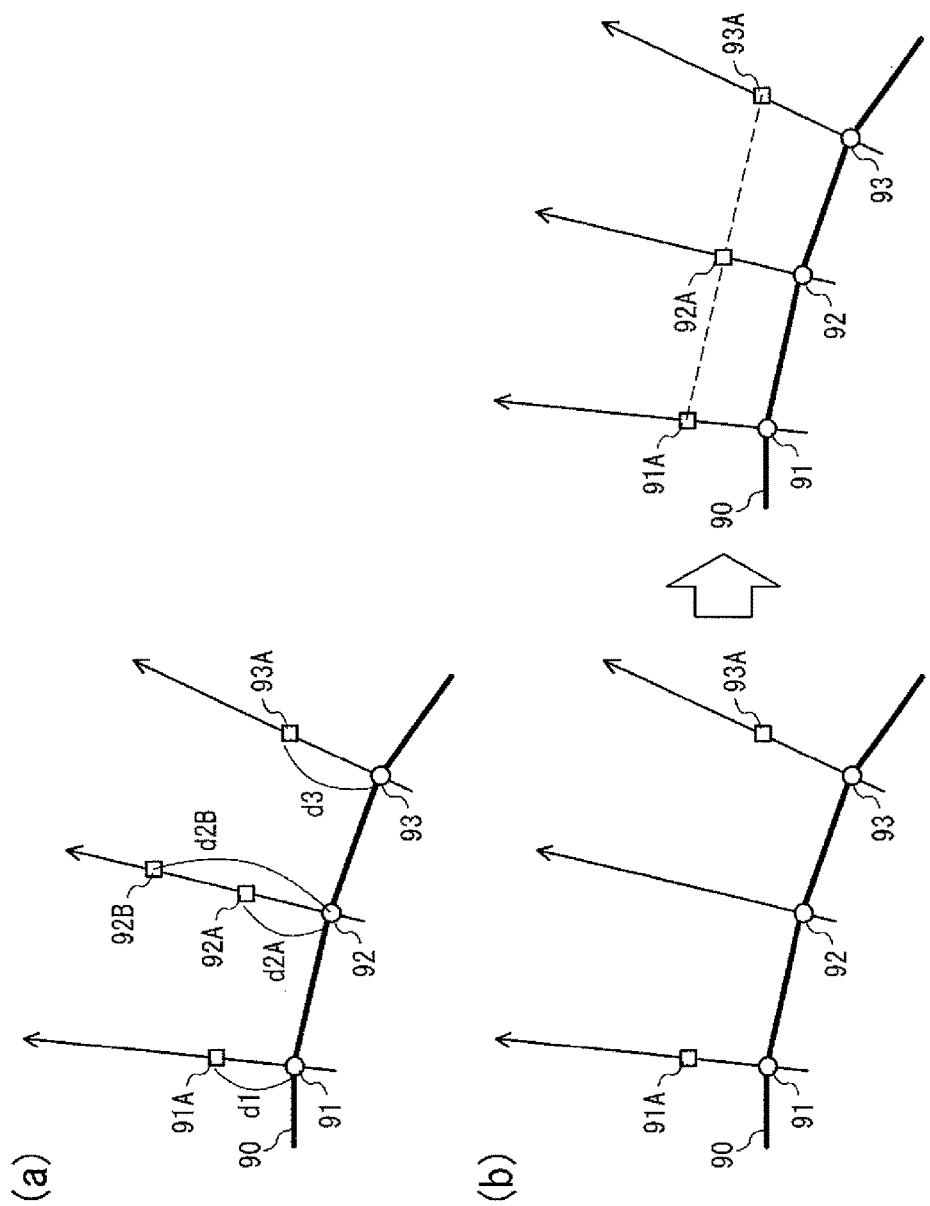
FIGS. 9(a)-(b) are diagrams for describing the processing in the second embodiment.

A specific example is shown in FIG. 9(*a*), which is an enlarged view of three base points 91 to 93 on an initial contour 90. Two edge point candidates 92A and 92B are detected for the focused base point 92. Here, the two base points 91 and 93 adjacent to the focused base point 92 are regarded as the peripheral base points, and it is assumed that only a single edge point 91A, 93A is detected for the peripheral base point 91, 93 (or that the corresponding edge point as already been determined). The distance between a base point and an edge point is represented by d1, d2A, d2B, and d3 in the diagram. Here, for example, the inspection region extraction unit 16 obtains a sum. SA of the differences between the distances when the candidate 92A is selected, and a sum SB of the differences between the distances when the candidate 92B is selected as follows:

$$SA=|d1-d2A|+|d3-d2A|$$

$$SB=|d1-d2B|+|d3-d2B|$$

The edge point candidate with the smallest sum of the distance differences is selected as the corresponding edge point of the focused base point 92. In the example of FIG. 9(a), the point 92A is selected.

The processing in Steps S802 to S804 described above is performed on all the base points, and the corresponding edge point is determined for a base point for which at least one edge point candidate is detected.

Then, the inspection region extraction unit 16 performs processing for a base point with no edge point candidate detected. Specifically, the focused base points are sequentially selected (Steps S806 and S809). For a focused base point with no corresponding edge point determined (Step S807), the corresponding edge point for the focused base point is generated by interpolating peripheral edge points (Step S808). FIG. 9(b) shows a specific example. When no edge point candidate is detected for the focused base point 92, the two base points 91 and 93 adjacent to the focused base point 92 are regarded as the peripheral base points. Then, the intersection between the line connecting the peripheral edge points 91A and 93A and the normal line of the initial contour 90 at the focused base point 92 is selected as the corresponding edge point 92A of the focused base point 92.

When the corresponding edge points are thus determined for all of the base points, the processing proceeds to Step S410 in FIG. 4. The processing thereafter is that in the same as the first embodiment.

The configuration of the second embodiment described above may provide the same advantageous effect as the first embodiment. The processing shown in FIG. 8 is an algorithm, in which the position of an edge point corresponding to the peripheral base point has a higher priority, and is favorably applied to an inspection target object with a relatively large individual difference and variation. In the second embodiment, only the neighboring base points on both sides of the focused base point are regarded as the peripheral base points. However, how the peripheral base point is selected is not limited to this. For example, one neighboring base point of the focused base point may be regarded as the peripheral base point. Furthermore, a plurality of base points in a predetermined range from the focused base point, such as two or three adjacent base points, may be regarded as the peripheral base points. The method shown in FIGS. 9(a)-(b) is merely an example. Any method can be utilized to evaluate the similarity of the distance from the base point, and to interpolate the peripheral edge points.

<Third Embodiment>

Figure 10:
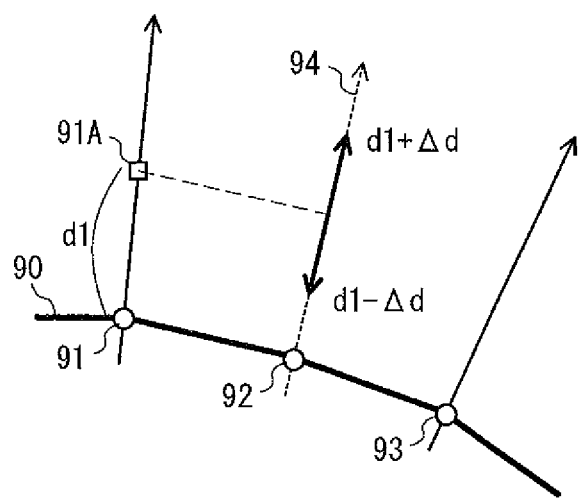
FIG. 10 is a diagram for describing processing in a third embodiment.

FIG. 10 shows a third embodiment of the present invention. In the third embodiment, the edge search range of the focused base point is narrowed down based on the positions of the peripheral edge points, to achieve even faster edge search processing. Aside from this, the configuration is similar to the other embodiments.

FIG. 10 is an enlarged view of the three base points 91 to 93 of the initial contour 90. Here, it is assumed that the processing of searching the corresponding edge point is performed sequentially on the base points 91 to 93 in this order. FIG. 10 shows a stage where a corresponding edge point 91A of the base point 91 has been determined, and thus the edge searching is performed on the next focused base point 92. In the first and the second embodiments, the edge searching for the focused base point 92 is performed on a search range 94, obtained from the inspection region defining information. In the third embodiment, the search range of the focused base point 92 is in the range of ±Δd from the distance d1, which is the distance between the corresponding edge point 91A and the peripheral base point 91 (bold arrow in FIG. 10). Neighboring base points are likely to have approximately the same variation of the contour position (specifically, the distance between the base point and the corresponding edge point). Thus, the unsatisfactory edge point detection is not substantially caused by thus narrowing down the search range.

With the method of the third embodiment, the search range is further narrowed down, and thus the time required for searching and determining edge points can be further shortened.

<Fourth Embodiment>

Figure 11:
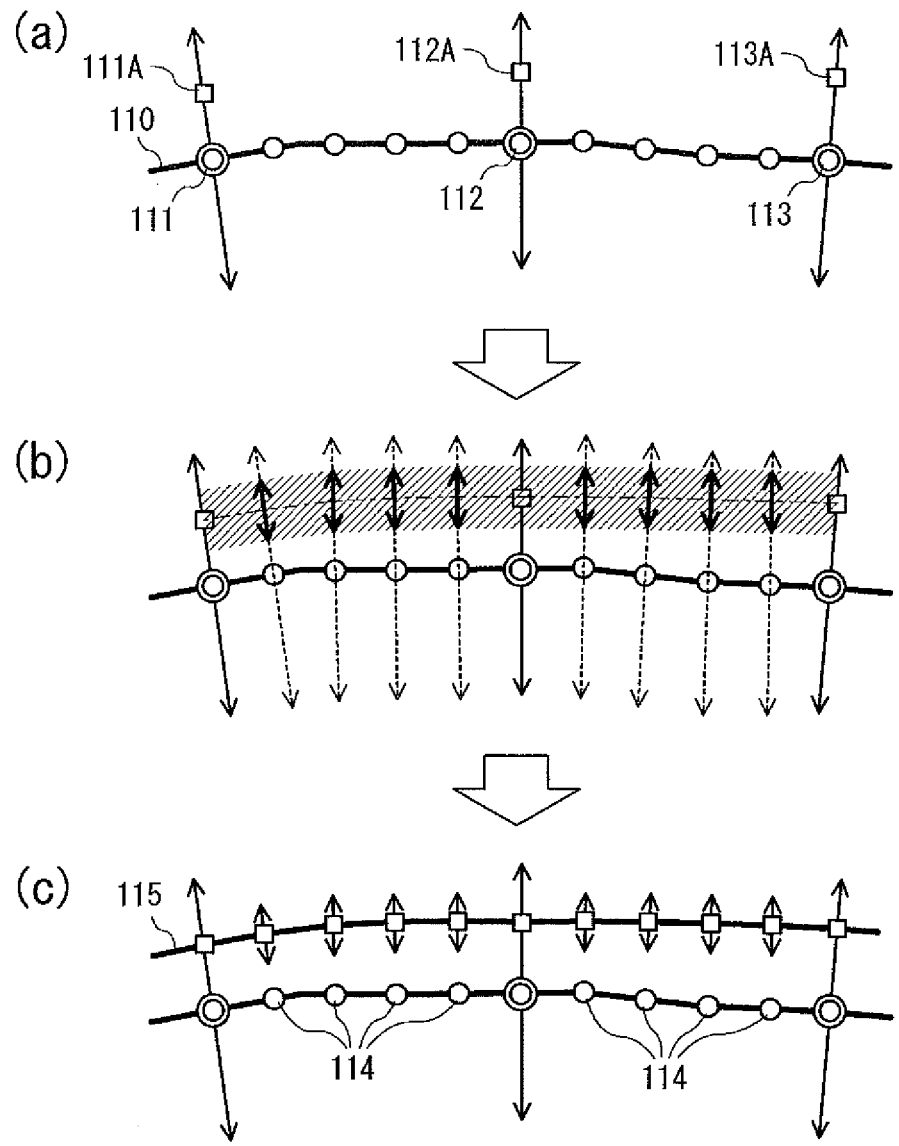
FIGS. 11(a)-(c) are diagrams for describing processing in a fourth embodiment.

FIGS. 11(a)-(c) show a fourth embodiment of the present invention. In the fourth embodiment, the edge searching is divided into a plurality of steps to be executed. Specifically, in the first step (rough searching step), base points are sparsely arranged, and the corresponding edge point of each base point is determined. In the next step (detailed searching step), the edge points are searched with the base points disposed more densely than in the rough searching step. In the detailed searching step, the search range is narrowed down based on the positions of the edge points determined in the rough searching step.

FIG. 11(a) shows the result of the rough searching step. In the rough searching step, the edge searching is performed for base points 111, 112, and 113 selected at an interval of every five base points, of all the base points of the initial contour 110. Reference signs 111A, 112A, and 113A each denote a detected corresponding edge point. Subsequently in the detailed searching step, as shown in FIG. 11(b), the search range is set as the range of ±Δd from the position of each of the corresponding edge points 111A, 112A, and 113A obtained by the rough searching (the region illustrated in hatching and bold arrows). Then, as shown in FIG. 11(c), the corresponding edge point is determined for each of the remaining base points 114, and thus, finally, a contour 115 of the inspection region is generated.

With the method of the fourth embodiment, the search range is further narrowed down, and thus the time required for searching and determining edge points can be further shortened.

<Fifth Embodiment>

Figure 12:
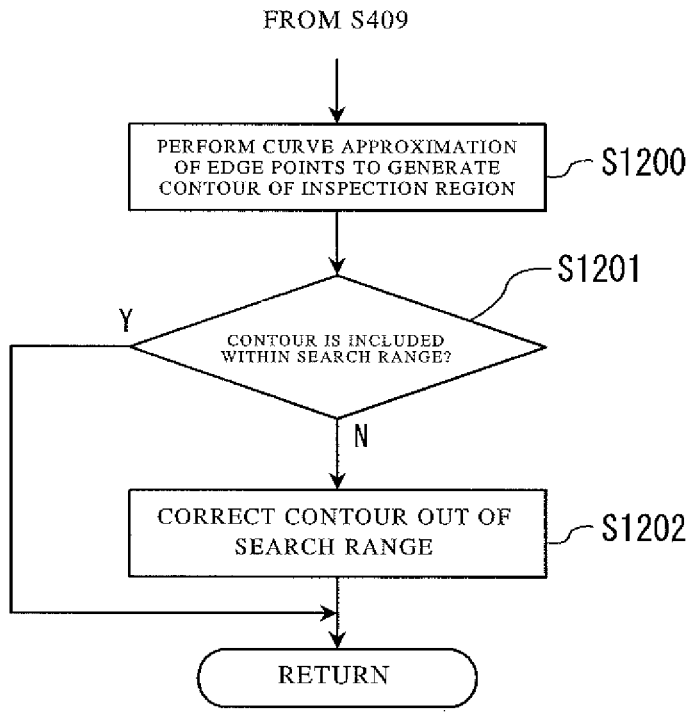
FIG. 12 is a diagram for describing processing in a fifth embodiment.

FIG. 12 shows a fifth embodiment of the present invention. In the fifth embodiment, the inspection region extraction unit 16 performs curve approximation for the sequence of corresponding edge points detected by the edge searching, to generate the contour of the inspection region (Step S1200). Specifically, a method may be employed, in which the sequence of corresponding edge points with an n-th spline curve or Bezier curve is approximated, for example. Alternatively, a method may be employed, in which segments (curve) are generated by grouping the corresponding edge points to several sequences of points, and by approximating the sequences with an arc or a line, and coupling the adjacent segments to generate the contour of the inspection region.

Then, the inspection region extraction unit 16 checks (Step S1201) whether the entire contour (approximate curve), generated in Step S1200, is included within the search range defined by the inspection region defining information (Step S1201). If a part of the contour is out of the search range, the inspection region extraction unit 16 corrects the contour so that the part is included within the search range (Step S1202). For example, the part of the contour out of the search range may be deformed to be along the extension (boundary) of the search range.

With the method of the fifth embodiment, smooth contour can be obtained, because the contour of the inspection region is generated from an approximate curve. Furthermore, with the correction to prevent the contour obtained by approximation from being disposed out of the search range, the contour of the inspection region can be prevented from being set at a position unintended by the user.

<Sixth Embodiment>

Figure 13:
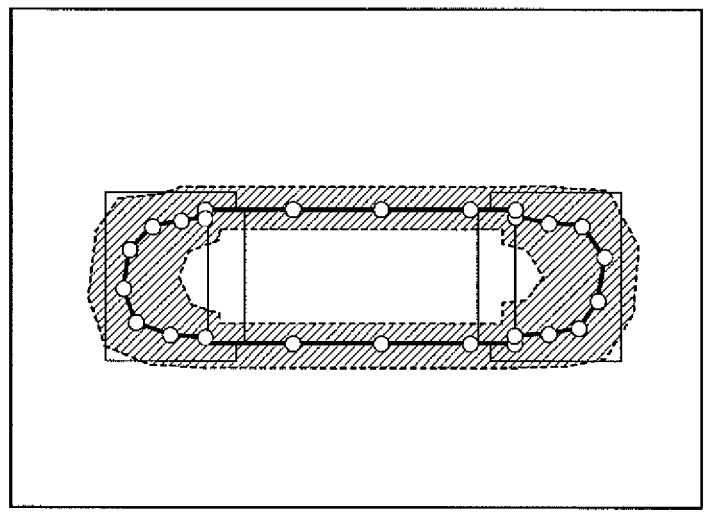
FIG. 13 is a diagram for describing processing in a sixth embodiment.

FIG. 13 shows an example of a setting screen for the inspection region defining information in a sixth embodiment of the present invention. In the first embodiment (FIGS. 7(a)-(c)), the number of base points and the width (pixel quantity) of the search range are each input with a numerical value. The base point interval and the search range width are uniform over the entire initial contour. However in the sixth embodiment, the arrangement of the base points (positions and density) and the search range width can be freely set by the user.

For example, a possible interface for designating how the base points are arranged includes: a method, in which the user designates the desired positions on the contour with the base points region disposed, by using a mouse and the like; a method of inputting coordinate values for disposing the base points; and a method, in which the setting tool 17 recommends arrangement examples of a plurality of base points, and the user selects the desired arrangement from the recommended examples. The user is also allowed to perform the operation such as adding the base points, displacing, or removing positions. In the case where the setting tool 17 recommends the base point arrangement (or the case the base points are automatically set), the base points may be disposed on a corner portion or a portion with large curvature, of the initial contour, for example. A possible interface for designating the density of the base points includes a method, in which the user designates the range of a part of the contour with a mouse and the like, and inputs the interval or the density of the base points within the designated range. The interval and the density of the base points may be input with numerical values, and may be adjusted with a GUI such as a slider.

A possible interface for designating the width of the search range includes a method, in which the outer and the inner contours of the search range (hatched portion) as shown in FIG. 13 are drawn with the approximate curve such as a spline curve, and the user can freely change the control points on the approximate curve with a mouse.

With the sixth embodiment, the following convenience can be obtained. A larger number of base point and a smaller interval provide an advantage that the contour of the inspection region can be accurately fit to the shape of the inspection target object, but also have the disadvantage that the processing time is longer. To address this, as described above, the means for setting the number, the interval, the arrangement, and the like of the base points is prepared. Thus, the user himself or herself can appropriately set the balance between the number of the base points and the like and the processing time, in accordance with the shape of the inspection target object, the tendency of the variation, or the like. Furthermore, the different search ranges can be set to positions on the contour. This enables a flexible range setting of setting a wide search range for a portion with large variation (solder portion and the like), and setting a narrow search range for a portion with small variation (main body portion of the electronic component), as shown in FIG. 13. As a result, the time required for inspection region extraction (edge searching) in the image inspection apparatus can be optimized, the processing time can be shortened.

<Other Embodiments>

The embodiments described above each represent a specific example of the present invention, and there is no intension to limit the scope of the present invention to the specific examples.

In one or more of the embodiments described above, when a plurality of edge point candidates are detected, the point closest to the base point is selected (first embodiment) and the point at the similar distance as the peripheral edge point is selected (second embodiment). Alternatively, other methods can be employed. For example, one of the detected edge point candidates with the largest edge intensity E may be selected as the corresponding edge point. Alternatively, a score of each edge point candidate (evaluation value regarded as a better value with larger edge intensity E and a higher similarity of the distance with the peripheral edge point) may be calculated from the edge intensity E and the similarity with the peripheral edge point in the distance used in the second embodiment. Thus, one with the highest score may be selected as the corresponding edge point. The score of this type may be calculated not only with the edge intensity and the similarity in distance, but also with other indexes. For example, an edge direction may be calculated for each edge point candidate, and the score may be evaluated with the direction that is the same as the direction (angle) of the peripheral edge point and the contour, largely weighted. An effect of removing noise (false edge) can be expected from these methods.

Figure 14:
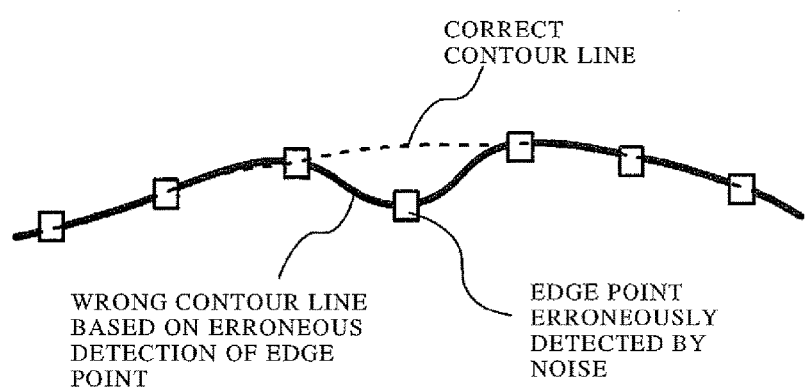
FIGS. 14(a)-(b) are diagrams for describing a method for determining a contour line through interpolation when a plurality of edge point candidates are detected.
Figure 14:
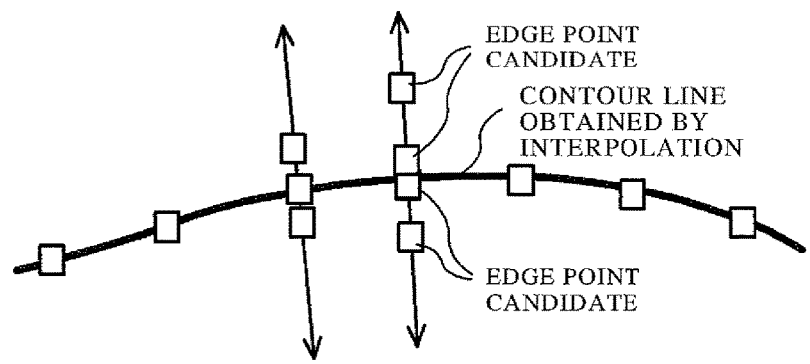

According to one or more embodiments of the present invention, the corresponding edge point is determined through interpolation, based on a plurality of edge point candidate. When an image includes noise (false edge) as shown in FIG. 14(a) for example, a point that is not the contour of the inspection target object might be detected as the edge point. Thus, when a plurality of edge point candidates are detected for a single base point, the interpolation may be performed through polynomial approximation with the least square error, by referring to a peripheral edge point (or the edge point candidates of the peripheral base point), so that an appropriate contour line is drawn. Here, as shown in FIG. 14(b), the position of the corresponding edge point is the intersection between the contour line obtained by the interpolation and the normal line of the base point. When the interpolation is performed through the polynomial approximation, according to one or more embodiments of the present invention, the focus is not only given on the position of the edge point candidate, and the each edge point candidate is weighted based on the edge point intensity or the edge direction, whereby the polynomial approximation such as weighted least square method is used. As the interpolation method, any methods such as spline interpolation and interpolation with an AR (Auto Regressive) model can be used. The interpolation based on the peripheral edge point and the edge point candidate of the peripheral base point may be applied to the interpolation for the corresponding edge point in a case where no edge point candidate is detected.

For example, it is assumed in one or more of the embodiments described above that the processing is performed in a unit of a pixel in an image. Alternatively, the edge searching may be performed in what is called sub-pixel accuracy to obtain more accurate contour. Specifically, the edge intensity on the normal line 63 shown in FIGS. 6(*c*) and (*d*) is evaluated in a sub-pixel accuracy more in detail than the pixel accuracy. The edge point and the coordinates on the contour calculated in the sub-pixel accuracy (that is, continuous value instead of discrete value) may be expressed with an a channel of the image. For example, when the contour crosses right in the middle of a pixel, the a value of the pixel is set to 0.5. Thus, the likelihood of the pixel as the inspection region is expressed with a predetermined gradation. The region of the sub pixel may be approximated with an interpolation curve such as the spline curve to be expressed. According to one or more embodiments of the present invention, the contour is smoothed in the sub-pixel accuracy.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE SIGNS LIST

1: image inspection apparatus
2: inspection target object (casing component)
10: apparatus main body, 11: image sensor, 12: display device, 13: storage device, 14: input device, 15: inspection processing unit, 16: inspection region extraction unit, 17: setting tool

The invention claimed is:
1. An image inspection method executed by an image inspection apparatus, the method comprising:
acquiring an inspection target object image obtained by capturing an image of an inspection target object;
reading, from a storage device that stores inspection region defining information created via an interactive setting tool that accepts one or more parameters for inspecting the target object while showing the image of the target object and a contour thereof in advance, the inspection region defining information;
extracting, as an inspection region image, a portion to be an inspection region from the inspection target object image, based on the inspection region defining information; and
performing inspection on the inspection target object by analyzing the inspection region image,
wherein the inspection region defining information comprises information defining an initial contour of the inspection region and information defining a range based on the initial contour as a search range for searching a contour of the inspection region,
wherein the range based on the initial contour as the search range includes distances both inside and outside of the initial contour, and
wherein the extracting comprises:
setting a plurality of base points on the initial contour;
performing edge search processing on a line that passes through each base point and intersects with the initial contour, within an region of the search range of the inspection target object image, to determine an edge point corresponding to each base point; and
connecting or approximating a plurality of the edge points respectively corresponding to the plurality of base points to generate the contour of the inspection region of the inspection target object image.

2. The image inspection method according to claim 1, wherein in the performing the edge search processing, when a plurality of edge point candidates are detected on a line passing through a certain base point, one of the plurality of candidates, closest to the base point, is selected as the edge point corresponding to the base point.

3. The image inspection method according to claim 1, wherein in the performing the edge search processing, when a plurality of edge point candidates are detected on a line passing through a certain base point, one of the plurality of candidates with a distance from the base point closest to a distance between a peripheral base point in a periphery of the base point and a peripheral edge point corresponding to the peripheral base point, is selected as the edge point corresponding to the base point.

4. The image inspection method according to claim 1, wherein in the performing the edge search processing, when no edge point is detected on a line passing through a certain base point, an edge point corresponding to the base point is set at the position that is the same as the base point.

5. The image inspection method according to claim 1, wherein in the performing the edge search processing, when no edge point is detected on a line passing through a certain base point, a plurality of peripheral edge points respectively corresponding to a plurality of peripheral base points in the periphery of the base point are interpolated to obtain a position of the edge point corresponding to the base point.

6. The image inspection method according to claim 1, wherein in the performing the edge search processing, a range in which an edge point corresponding to a certain base point is searched is obtained by narrowing down the search range, based on a position of the peripheral edge point corresponding to a peripheral base point in the periphery of the base point.

7. The image inspection method according to claim 1, wherein the performing the edge search processing comprises:
(a) determining a corresponding edge point for each of a plurality of base points sparsely disposed on the initial contour; and
(b) determining the corresponding edge point for each of a plurality of base points more densely disposed than in the step (a), and
wherein in the step (b), a range in which an edge point corresponding to a certain base point is searched is obtained by narrowing down the search range, based on a position of the edge point determined in the step (a).

8. The image inspection method according to claim 1, wherein in the connecting or approximating the plurality of the edge points, whether a generated contour is included within the search range is determined, and when the contour has a portion outside the search range, the contour is corrected so that the portion is included within the search range.

9. An inspection region setting method for setting the inspection region defining information for an image inspection apparatus configured to execute the image inspection method according to claim 1, the method comprising:

acquiring by a computer a sample image of an inspection target object and an inspection region set to the sample image;

extracting by the computer a contour of the inspection region;

allowing by the computer a user to set a range in which the contour of the inspection region is variable; and generating by the computer inspection region defining information comprising information defining an initial contour and information defining a search range, based on the contour of the inspection region and the range set by the user.

10. The inspection region setting method according to claim 9, wherein in the allowing the user to set the range, different ranges are settable at positions on the contour of the inspection region.

11. The inspection region setting method according to claim 9, wherein information defining the initial contour comprises information defining positions of the plurality of base points set on the initial contour when the edge search processing in the image inspection method is performed, and wherein the inspection region setting method further comprises:

allowing by the computer the user to set a quantity, interval, or arrangement of the base points; and determining by the computer the positions of the plurality of the base points set on the initial contour, based on the quantity, the interval, or the arrangement of the base points set by the user.

12. A program stored on a non-transitory computer-readable medium that causes an image inspection apparatus to perform:

acquiring an inspection target object image obtained by capturing an image of an inspection target object;

reading, from a storage device that stores inspection region defining information created via an interactive setting tool that accepts one or more parameters for inspecting the target object while showing the image of the target object and a contour thereof in advance, the inspection region defining information;

extracting, as an inspection region image, a portion to be an inspection region from the inspection target object image, based on the inspection region defining information; and performing inspection on the inspection target object by analyzing the inspection region image, wherein the inspection region defining information comprises information defining an initial contour of the inspection region and information defining a range based on the initial contour as a search range for searching a contour of the inspection region, wherein the range based on the initial contour as the search range includes distances both inside and outside of the initial contour, and wherein the extracting comprises:

setting a plurality of base points on the initial contour;

performing edge search processing on a line that passes through each base point and intersects with the initial contour, within an region of the search range of the inspection target object image, to determine an edge point corresponding to each base point; and connecting or approximating a plurality of the edge points respectively corresponding to the plurality of base points to generate the contour of the inspection region of the inspection target object image.

13. An image inspection apparatus comprising:

a processor, comprising:

an acquisition section that acquires an inspection target object image obtained by capturing an image of an inspection target object;

a setting reading section that reads, from a storage device that stores inspection region defining information created via an interactive setting tool that accepts one or more parameters for inspecting the target object while showing the image of the target object and a contour thereof in advance, the inspection region defining information;

an inspection region extractor that extracts, as an inspection region image, a portion to be an inspection region from the inspection target object image, based on the inspection region defining information; and an inspection processor that performs inspection on the inspection target object by analyzing the inspection region image, wherein the inspection region defining information comprises information defining an initial contour of the inspection region and information defining a range based on the initial contour as a search range for searching a contour of the inspection region, wherein the range based on the initial contour as the search range includes distances both inside and outside of the initial contour, and wherein the inspection region extractor comprises:

a base point setting section that sets a plurality of base points on the initial contour;

an edge searching section that performs edge search processing on a line that passes through each base point and intersects with the initial contour, within an region of the search range of the inspection target object image, to determine an edge point corresponding to each base point; and a contour generator that connects or approximates a plurality of the edge points respectively corresponding to the plurality of base points to generate the contour of the inspection region of the inspection target object image.

14. An inspection region setting device configured to set the inspection region defining information for an image inspection apparatus according to claim 13, wherein the processor further comprises:

an acquisition section that acquires a sample image of an inspection target object, and an inspection region set to the sample image;

a contour extractor that extracts a contour of the inspection region;

a range setting section that allows a user to set a range in which the contour of the inspection region is variable; and a defining information generator that generates inspection region defining information comprising information defining an initial contour and information defining a search range, based on the contour of the inspection region and the range set by the user.

* * * * *